United States Patent
Ding et al.

(10) Patent No.: US 9,856,524 B2
(45) Date of Patent: Jan. 2, 2018

(54) LYOPHILIZED INTEGRATED COMPOSITION FOR STORAGE AND MANIPULATION OF PYROPHOSPHOROLYSIS ACTIVATED POLYMERIZATION

(71) Applicants: Shaofeng Ding, Santa Fe Springs, CA (US); Qiang Liu, Upland, CA (US)

(72) Inventors: Shaofeng Ding, Santa Fe Springs, CA (US); Qiang Liu, Upland, CA (US)

( * ) Notice: Subject to any disclaimer, the term of this patent is extended or adjusted under 35 U.S.C. 154(b) by 246 days.

(21) Appl. No.: 14/559,920

(22) Filed: Dec. 4, 2014

(65) Prior Publication Data
US 2016/0160273 A1   Jun. 9, 2016

(51) Int. Cl.
*C12Q 1/68* (2006.01)

(52) U.S. Cl.
CPC ......... *C12Q 1/6848* (2013.01); *C12Q 1/6844* (2013.01)

(58) Field of Classification Search
None
See application file for complete search history.

(56) References Cited

U.S. PATENT DOCUMENTS

| | | | | |
|---|---|---|---|---|
| 8,574,846 B2 * | 11/2013 | Piepenburg | .......... | C12Q 1/6844 435/6.12 |
| 2007/0219361 A1 * | 9/2007 | Bodepudi | .............. | C07H 21/00 536/23.1 |

OTHER PUBLICATIONS

Li et al. (PNAS, 1999, vol. 96, p. 9491-9496).*
Lee et al. (J Clin Virol, 2004, vol. 31, p. 275-282).*

* cited by examiner

*Primary Examiner* — Stephanie K Mummert

(57) ABSTRACT

The invention provides a method for lyophilizing integrated composition of pyrophosphorolysis activated polymerization (PAP) in an aqueous solution. It also provides lyophilized integrated PAP composition. Except for nucleic acid template, the integrated composition contains all components. For manipulation, simply add nucleic acid template in an aqueous solution to start amplification. In addition to the easy manipulation, the lyophilized integrated composition can be stored for prolonged period at ambiguous temperature.

9 Claims, No Drawings

```
                            SEQUENCE LISTING

<160> NUMBER OF SEQ ID NOS: 12

<210> SEQ ID NO 1
<211> LENGTH: 27
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is FAM-dT

<400> SEQUENCE: 1
caccaactgt ttcggttggc tttggng                                          27

<210> SEQ ID NO 2
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 2
cttggtctca aagattccag aagtcaggan                                       30

<210> SEQ ID NO 3
<211> LENGTH: 30
<212> TYPE: DNA
<213> ORGANISM: Aids-associated retrovirus
<220> FEATURE:
<221> NAME/KEY: misc_feature
<222> LOCATION: (30)..(30)
<223> OTHER INFORMATION: n is dideoxyT

<400> SEQUENCE: 3
agtgggggga catcaagcag ccatgcaaan                                       30

<210> SEQ ID NO 4
<211> LENGTH: 27
<212> TYPE: DNA
<213> ORGANISM: Aids-associated retrovirus
<220> FEATURE:
<221> NAME/KEY: misc_feature
<222> LOCATION: (25)..(25)
<223> OTHER INFORMATION: n is FAM-dT

<400> SEQUENCE: 4
gaaccatatg tcacttcccc ttggntc                                          27

<210> SEQ ID NO 5
<211> LENGTH: 30
```

```
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 5
tgggtatagg ggcgaaagac taatcgaacn                                30

<210> SEQ ID NO 6
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 6
ctgagggaaa cttcggaggg aaccagctan                                30

<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyG

<400> SEQUENCE: 7
gcagcatgtc aagatcacag attttgggcn                                30

<210> SEQ ID NO 8
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a dideoxyC

<400> SEQUENCE: 8
ctttctcttc cgcacccagc agtttggccn                                30

<210> SEQ ID NO 9
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyA

<400> SEQUENCE: 9
caagatcaca gattttgggc tggccaaacn                                30

<210> SEQ ID NO 10
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 10
```

```
catggtattc tttctcttcc gcacccagcn                                    30

<210> SEQ ID NO 11
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyT

<400> SEQUENCE: 11
ctgcctcacc tccaccgtgc agctcatcan                                    30

<210> SEQ ID NO 12
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is dideoxyA

<400> SEQUENCE: 12
aggaggcagc cgaagggcat gagctgcn                                      28
```

LYOPHILIZED INTEGRATED COMPOSITION FOR STORAGE AND MANIPULATION OF PYROPHOSPHOROLYSIS ACTIVATED POLYMERIZATION

SEQUENCE LISTING

This application is being filed along with a Sequence Listing and its electronic format entitled SequenceListing.txt.

BACKGROUND OF THE INVENTION

Field of the Invention

The present invention relates to the field of molecular biology and nucleic acid amplification. A composition for pyrophosphorolysis activated polymerization (PAP) is integrated by lyophilization. The lyophilized integrated composition is easily stored and manipulated.

Description of the Prior Art

PAP Technology for Nucleic Acid Amplification

Pyrophosphorolysis activated polymerization (PAP) is a method for nucleic acid amplification where pyrophosphorolysis and polymerization are serially coupled by DNA polymerase using 3' blocked primers[1, 2]. A primer is blocked at the 3' end with a non-extendable nucleotide (3' blocker), such as a dideoxynucleotide, and cannot be directly extended by DNA polymerase. When the 3' blocked primer anneals to its complementary DNA template, DNA polymerase can remove the 3' blocker from the 3' blocked primer in the presence of pyrophosphate or its analog, which reaction is called pyrophosphorolysis. The DNA polymerase can then extend the 3' unblocked primer on the DNA template. In addition to references cited herein, PAP has been described in U.S. Pat. Nos. 6,534,269, 7,033,763, 7,105,298, 7,238,480, 7,504,221, 7,914,995, and 7,919,253.

The serial coupling of pyrophosphorolysis and extension using the 3' blocked primer in PAP results in an extremely high selectivity[2, 3] because a significant nonspecific amplification (Type II error) requires mismatch pyrophosphorolysis followed by mis-incorporation by the DNA polymerase, an event with a frequency estimated to be $3.3 \times 10^{-11}$.

The bi-directional form of PAP (Bi-PAP) is especially suitable for allele-specific amplification that uses two opposing 3' blocked primers with a single-nucleotide overlap at their 3' ends[3, 4]. Bi-PAP can detect one copy of a mutant allele in the presence of $10^9$ copies of the wild type DNA without false positive amplifications.

DNA-PAP

PAP was initially tested with Tfl and Taq polymerases using DNA template of the human dopamine D1 gene, proving the principle that DNA-dependent DNA pyrophosphorolysis and DNA-dependent DNA polymerization can be serially coupled[1]. The efficiency of PAP was greatly improved using TaqFS, a genetically engineered polymerase comprising a F667Y mutation, which were demonstrated using other DNA templates[4].

RNA-PAP

RNA-PAP was developed that can directly amplify RNA template without additional treatment. RNA-PAP brings in a new mechanism for amplification of RNA template in which RNA-dependent DNA pyrophosphorolysis removes 3' blocker such as 3' dideoxynucleotide from a blocked primer when hybridized to RNA template, and then RNA-dependent DNA polymerization extends the activated primer. Due to this serial coupling, RNA-PAP has high selectivity against mismatches on the RNA template, providing highly specific amplification of RNA template (US Patent Application Publication No. 20140186840).

Lyophilization

Lyophilization or freeze-drying is a dehydration process by freezing a material and then reducing the surrounding pressure to allow the frozen water in the material to sublimate directly from solid phase to gas phase. This process has been used for stabilizing reverse transferase and RNA polymerase (U.S. Pat. No. 5,614,387), lyophilizing PCR reagents (U.S. Pat. Nos. 5,861,251, 6,153,412, WO Publication No. 2005103277, EP Patent No. 2,202,302), and drying dye-terminator sequencing reagents (U.S. Pat. No. 7,407,747).

However, the result of lyophilization is still largely unpredictable particularly in the case of multiplex components because of fragile balance and interaction among them. For example, it was reported that inclusion of primers in dried mixture inactivates Taq polymerase (EP Patent No. 2,202,302), and Magnesium ion initiates nonspecific reaction leading to false positive amplification.

Manipulation of PAP Reaction

Aqueous PAP reaction contains many components of a reaction buffer, pyrophosphate, dNTPs, 3' blocked primers, a polymerase, and a nucleic acid template which are stored in a number of different tubes. For manipulation, the PAP components from the different tubes are pipetted into a tube, which is tedious, error-prone, and time-consuming.

Advantages of the Invention

It is convenient to contain or integrate all the PAP components except for nucleic acid template in only one tube. However, in the aqueous integrated PAP composition the polymerase is unstable and dNTPs are easily degraded particularly when stored at room temperature. To solve this problem, a method for lyophilizing aqueous integrated composition of PAP was developed so that the lyophilized integrated composition is easily manipulated and stored for prolonged period at ambiguous temperature.

SUMMARY OF THE INVENTION

A method for lyophilizing integrated composition for PAP comprises: a) providing integrated composition in an aqueous solution comprising a mixture of I) a reaction buffer, 3' blocked primers, deoxynucleotide triphosphates and pyrophosphate, a fluorescent dye, a nucleic acid polymerase, but not nucleic acid template, and II) a non-reducing disaccharide, and b) lyophilizing the aqueous solution into dried integrated composition, so that the integrated composition can be easily stored and manipulated.

In the aqueous integrated composition, the reaction buffer comprises Tis-HCl, $(NH_4)_2SO_4$, and $Mg^{++}$, the deoxynucleotide triphosphates and pyrophosphate are dATP, dTTP, dGTP, dCTP, $Na_4O_7P_2$ or their analogs, the fluorescent dye is SybrGreen I or Fam attached to a primer, and the polymerase is Taq polymerase comprising a F667Y amino acid mutation.

In the aqueous integrated composition, the disaccharide comprises trehalose, sucrose, maltose, cellobiose, lactose, or lactulose.

The aqueous integrated composition further comprises BSA, a polyol selected from a group consisting of Ficoll, Dextran, polyethylene glycol (PEG), and Polyvinylpyrrolidone (PVP), and a detergent selected from a group consisting of Tween 20 and NP-40.

The method for lyophilizing integrated composition for PAP further comprises a step c) solubilizing the lyophilized integrated composition by addition of a nucleic acid template in aqueous solution.

A lyophilized integrated composition for PAP prepared in accordance with the method for lyophilizing integrated composition described above.

The lyophilized integrated composition is solubilized by addition of an aqueous solution containing a nucleic acid template.

A method to perform PAP amplification comprises: a) solubilizing a lyophilized integrated composition by addition of an aqueous solution comprising a nucleic acid template to the lyophilized integrated composition, wherein the lyophilized integrated composition comprises reaction buffer components, 3' blocked primers, deoxynucleotide triphosphates and pyrophosphate, a fluorescent dye, a nucleic acid polymerase, and a non-reducing disaccharide, but not nucleic acid template, and b) performing a thermocycling for amplification.

In the lyophilized integrated composition, the reaction buffer components comprise Tis-HCl, $(NH_4)_2SO_4$, and $Mg^{++}$. The deoxynucleotide triphosphates and pyrophosphate are dATP, dTTP, dGTP, dCTP, $Na_4O_7P_2$ or their analogs. The fluorescent dye is SybrGreen I or Fam attached to a primer. The polymerase is Taq polymerase comprising a F667Y amino acid mutation.

In the lyophilized integrated composition, the disaccharide comprises trehalose, sucrose, maltose, cellobiose, lactose, or lactulose.

The lyophilized integrated composition further comprises BSA, a polyol selected from a group consisting of Ficoll, Dextran, polyethylene glycol (PEG), and Polyvinylpyrrolidone (PVP), and a detergent selected from a group consisting of Tween 20 and NP-40.

DETAILED DESCRIPTION OF THE INVENTION

Terminology

Unless defined otherwise, all technical and scientific terms used herein have the same meaning as commonly understood by one of ordinary skill in the art.

PCR refers to polymerase chain reaction.

Pyrophosphorolysis is the reverse reaction of deoxyribonucleic acid polymerization. In the presence of pyrophosphate, the 3' nucleotide is removed by a polymerase from duplex DNA to generate a triphosphate nucleotide and a 3' unblocked duplex DNA: $[dNMP]_n + PPi \rightarrow [dNMP]_{n-1} + dNTP$[5].

Polymerase or nucleic acid polymerase refers to a polymerase characterized as polymerization or extension of deoxyribonucleic acids. It can be DNA template dependent or RNA template dependent.

3' blocked primer refers to an oligonucleotide with a 3' non-extendable nucleotide (3' blocker), such as a dideoxynucleotide. The 3' nucleotide could not be directly extended, but it can be removed by pyrophosphorolysis and then the unblocked primer can be extended by polymerase.

PAP refers to pyrophosphorolysis activated polymerization.

Thermostable enzyme refers to an enzyme that is heat stable or heat resistant.

Protein mutation refers to a change in amino acid residue at a location of a protein, like Taq polymerase. The change in amino acid residue is defined with respect to a naturally occurring protein. A protein having a mutation is referred to as a "mutant" protein.

TaqFS is a genetic engineered form of Taq polymerase containing G46E and F667Y amino acid changes compared with wild type sequence.

Freeze-drying, also known as lyophilization, is a dehydration process by freezing the material and then reducing the surrounding pressure to allow the frozen water in the material to sublimate directly from the solid phase to the gas phase.

Dry composition refers to a composition that is substantially free of solvent.

Lyophilized PAP refers to PAP using lyophilized composition.

Lyophilization of Integrated Composition for PAP

For lyophilization, an integrated PAP composition in an aqueous solution can be divided into a PAP essential component, a lyophilization essential component, and other components.

The PAP essential component in the aqueous solution comprises a reaction buffer, 3' blocked primers, deoxynucleotide triphosphates, pyrophosphate, a nucleic acid polymerase, and a fluorescent dye if real time detection is needed. The concentration and corresponding volume of PAP essential component were found critical because they affected not only the sublimate in lyophilization but also the component stability. Their optimal values varied from 2× to 4× concentrations and corresponding ½ to ¼ volumes compared with those when the solubilized reaction mixture starts amplification (1× concentration and 20 μl volume).

The lyophilization essential component in the aqueous solution should be compatible to the PAP essential component, and can keep the PAP essential component stable. We found that a non-reducing disaccharide, such as trehalose, sucrose, maltose, cellobiose, lactose, or lactulose, was substantially sufficient to function effectively. The critical concentrations varied from 200 μM to 400 μM, no matter what the volumes of the aqueous solution were.

The other components in the aqueous solution, which may stimulate, comprise polyols, such as Ficoll-400, Dextran, polyethylene glycol-8000 (PEG), and Polyvinylpyrrolidone (PVP) at various concentrations from 0.05 to 4%, BSA protein from 25 to 100 ng/μl, and detergents, such as Tween 20 from 0.0125-0.05%.

For demonstration, PAP assays of the GNAS, HIV, rDNA and EGFR genes were examined (Table 1). We found that the lyophilized samples showed efficient and specific amplifications even after stored at 50° C. for up to six days, indicating the success. The optimal integrated PAP composition for lyophilization is described in Materials and Methods unless stated otherwise.

Example 1

Materials and Methods
Preparation of Primers

Primers with 6-FAM labeled dT near the 3' end were chemically synthesized in 3'-5' direction and purified by HPLC by Integrated DNA Technologies.

3' ddCMP blocked primers were chemically synthesized in 3'-5' direction and purified by HPLC by Integrated DNA Technologies.

3' ddAMP, ddTMP, and ddGMP blocked primers were synthesized enzymatically by adding ddATP, ddTTP and ddGTP to the 3' ends of oligodeoxynucleotides by terminal transferase[1, 4]. Then they were purified by 7M urea/16% polyacrylamide gel electrophoresis. The amount of each recovered primer was determined by UV absorbance at 260 nm (Table 1).

TABLE 1

List of primers

| Gene | Name | Sequence (5' to 3')(SEQ ID NO:) | 3' end | Product size (bp) | Starting template |
|---|---|---|---|---|---|
| GNAS | GNAS-Forward | CACCAACTGTTTCGGTTG GCTTTGG/FAM-dT/G [a] (1) | dGMP | 108 | Genomic DNA |
|  | GNAS-Reverse | CTTGGTCTCAAAGATTCC AGAAGTCAGGAddC (2) | ddCMP |  |  |
| HIV | HIV-Forward | AGTGGGGGACATCAAG CAGCCATGCAAAddT (3) | ddTMP | 145 | Recombinant plasmid DNA |
|  | HIV-Reverse | GAACCATATGTCACTTCC CCTTGG/FAM-dT/TC (4) | dCMP |  |  |
| rDNA | rDNA-Forward | TGGGTATAGGGGCGAAA GACTAATCGAACddC (5) | ddCMP | 66 | Genomic DNA |
|  | rDNA-Reverse | CTGAGGGAAACTTCGGA GGGAACCAGCTAddC (6) | ddCMP |  |  |
| EGFR | EGFR-L858R-Forward | GCAGCATGTCAAGATCAC AGATTTTGGGCddG (7) | ddGMP | 59 | Recombinant plasmid DNA |
|  | EGFR-L858R-Reverse | CTTTCTCTTCCGCACCCA GCAGTTTGGCCddC (8) | ddCMP |  |  |
| EGFR | EGFR-L861Q-Forward | CAAGATCACAGATTTTGG GCTGGCCAAACddA (9) | ddAMP | 59 | Recombinant plasmid DNA |
|  | EGFR-L861Q-Reverse | CATGGTATTCTTTCTCTTC CGCACCCAGCddT (10) | ddTMP |  |  |
| EGFR | EGFR-L790M-Forward | CTGCCTCACCTCCACCGT GCAGCTCATCAddT (11) | ddTMP | 57 | Recombinant plasmid DNA |
|  | EGFR-L790M-Reverse | AGGAGGCAGCCGAAGGG CATGAGCTGCddA (12) | ddAMP |  |  |

Footnotes of Table 1.
[a] CACCAA is a tail attached to the 5' end of the primer. /FAM-dT/ means Fluorescein labeled dT.

Preparation of Templates

Genomic DNA was extracted from blood white cells using QIAamp Blood Mini Kit according to Qiagen's protocol. Recombinant plasmid DNA was constructed by inserting into pUC57 vector a 100-400 bp target DNA segment which was chemically synthesized or PCR amplified. After transformed into E. coli, the recombinant plasmid DNA was extracted using QIAamp Plasmid Mini Kit according to Qiagen's protocol. The eluted DNA was dissolved in TE buffer (10 mM Tris-HCl, 0.1 mM EDTA, pH8.0) and its amount was determined by UV absorbance at 260 nm.

Preparation of Integrated PAP Composition for Lyophilization

Before lyophilization, an aqueous solution of 5 µl was prepared that contained 352 mM Tris-HCl (pH 8.0 at 25° C.), 40 mM $(NH_4)_2SO_4$, 4.8-10 mM $MgCl_2$, 100 or 180 µM each dNTPs (dATP, dTTP, dGTP and dCTP), 0.4 µM each primers, 360 µM $Na_4PP_i$, 0.4× SybrGreen I dye, 0.04% Twee-20, 2 units of polymerase, 200-400 mM trehalose, 0-0.4% Ficoll-400, 50-100 µg/ml BSA, and 1 mM DTT. The aqueous solution was put into single tubes, 8-well strips, or 96-well plates.

Another aqueous solution of 10 µl was prepared that contained 176 mM Tris-HCl (pH 8.0 at 25° C.), 20 mM $(NH_4)_2SO_4$, 2.4-5 mM $MgCl_2$, 50 or 90 µM each dNTPs (dATP, dTTP, dGTP and dCTP), 0.2 µM each primers, 180 µM $Na_4PP_i$, 0.2× SybrGreen I dye, 0.02% Twee-20, 2 units of polymerase, 200-400 mM trehalose, 0.2% Ficoll-400, 100 µg/ml BSA, and 0.5 mM DTT. The aqueous solution was put into single tubes, 8-well strips, or 96-well plates.

Lyophilization Procedure

Lyophilization process was performed using a VFD2000 Freeze Dryer (Beijing Bo Kang Experimental Medical Instrument, China). After quickly frozen at −50° C. for 2 hours, the samples were vacuumed at 10-15 Pa pressure and kept at −45° C. for 20 hours, at −20° C. for 1 hour, at 5° C. for 1 hour, and at 30° C. for 1 hour.

Storage Stability of the Lyophilized Integrated PAP Composition

After lyophilization, the dried samples were stored at −20° C., 37° C., or 50° C. for periods of time to test the stability.

Solubilization of Lyophilized Integrated Composition for PAP Amplification

An aqueous solution containing DNA template was added to the lyophilized integrated composition to the final volume of 20 µl. The solubilized reaction mixture contained 88 mM Tris-HCl (pH 8.0 at 25° C.), 10 mM $(NH_4)_2SO_4$, 1.2-2.5 mM $MgCl_2$, 25 or 45 µM each dNTPs (dATP, dTTP, dGTP and dCTP), 0.1 µM each primers, 90 µM $Na_4PP_i$, 0.1× SybrGreen I dye, 0.01% Twee-20, 2 units of polymerase, 100-200 mM trehalose, 0.1% Ficoll-400, 25-50 µg/ml BSA, and 0.1 mM DTT, as well as the DNA template.

Thermocycling

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

A cycling entailed 96° C. for 12 seconds, 60° C. for 30 seconds, 64° C. for 30 seconds, and 68° C. for 30 seconds for a total of 40 cycles; or another cycling entailed 96° C. for 12 seconds, 64° C. for 45 seconds, and 68° C. for 45 seconds for a total of 40 cycles. A denaturing step of 96° C. for 2 min was added before the first cycle.

To confirm the amplified product, melting curving analysis was followed from 68° C. to 95° C. with increment 0.5° C. and holding 5 seconds to confirm the specific amplified product.

Example 2

A PAP assay was designed to amplify the wild type sequence of the GNAS gene (Table 1). A LUX (Light Upon eXtension) primer labeled with FAM near the 3' end was used to emit real-time fluorescence signals[6]. Once primer was annealed and extended into products, LUX emits more fluorescent signal.

The lyophilized integrated PAP composition was prepared as in Materials and Methods. Factors of 200 µm to 400 µm trehalose, 5 µl and 10 µl of the aqueous solution, and 0% to 0.4% Ficoll were tested in Table 2. After lyophilization, the samples were stored at −20° C., the stability did not change substantially. In order to accelerate, the samples were stored at 50° C. Before cycling, 20 ng of genomic DNA in TE buffer was added to 20 µl volume.

To assess the PAP amplification performance, Ct and RFU were measured. Ct is threshold cycle and RFU is the highest fluorescent signal subtracts baseline in random units. With 250 µM, 300 µM, and 400 µM trehalose, Ct and RFU had efficient amplifications, showing the lyophilized integrated composition stable at 50° C. for six days. In addition, $T_m$ was also measured within 82-83° C., showing the specificity.

However, with 200 µM trehalose (Mix 7), Ct and RFU had inefficient amplification when stored at 50° C. for six days, showing the insufficient effect of low trehalose concentration, but not of Ficoll.

Example 3

A PAP assay was designed to amplify HIV DNA (Table 1). A LUX (Light Upon eXtension) primer labeled with FAM near the 3' end was used to emit real-time fluorescence signals[6].

The lyophilized integrated PAP composition was prepared as in Materials and Methods. Factors of 300 µm and 400 µm trehalose, and 5 µl and 10 µl of the aqueous solution were tested (Table 3). After lyophilization, the samples were stored at 50° C. for 0, 2, 4 and 6 days. Before cycling, 10,000 copies of the recombinant plasmid DNA in TE buffer were added to 20 µl volume.

To assess the PAP amplification performance, Ct and RFU was measured. For each mix, Ct and RFU had similar values among different days, showing the stability at 50° C. for six days. In addition, $T_m$ was also measured within 83±1° C., showing the specificity.

TABLE 2

Stability test in the GNAS gene

| Aqueous solution[a] | Performance | Before | Lyophilization After | | |
|---|---|---|---|---|---|
| | | 0 days | 50° C. for 2 days | 50° C. for 4 days | 50° C. for 6 days |
| Mix 1 | Ct | 23.94 | 24.39 | 24.17 | 24.4 | 24.63 |
| | RFU | 800 | 620 | 690 | 660 | 620 |
| Mix 2 | Ct | 24.29 | 24.55 | 24.3 | 24.02 | 24.16 |
| | RFU | 700 | 560 | 590 | 620 | 640 |
| Mix 3 | Ct | 24.23 | 24.48 | 24.41 | 24.56 | 24.73 |
| | RFU | 750 | 600 | 560 | 530 | 520 |
| Mix 4 | Ct | 24.18 | 24.18 | 24.33 | 24.54 | 23.83 |
| | RFU | 700 | 560 | 540 | 530 | 600 |

| | | 50° C. for 1 day | 50° C. for 2 days | 50° C. for 3 days | 50° C. for 6 days |
|---|---|---|---|---|---|
| Mix 5 | Ct | 23.94 | 23.90 | 23.50 | 24.11 |
| | RFU | 560 | 620 | 660 | 570 |
| Mix 6 | Ct | 24.16 | 23.89 | 23.85 | 24.25 |
| | RFU | 660 | 660 | 630 | 600 |
| Mix 7 | Ct | 24.18 | 24.08 | 23.85 | 24.32 |
| | RFU | 650 | 590 | 570 | 370 Curve not steep |

Footnotes of Table 2.
[a]Mix 1 and Mix 2 comprised in 10 µl of the aqueous solution 176 mM Tris-HCl (pH 8.0 at 25° C.), 20 mM (NH$_4$)$_2$SO$_4$, 5 mM MgCl$_2$, 90 µM each dNTPs, 0.2 µM each GNAS primers, 180 µM Na$_4$PP$_i$, 2 units of polymerase, 0.02% Twee-20, 50 µg/ml BSA, 0.5 mM DTT, and 0.20% Ficoll-400. In addition, Mix 1 contained 300 mM and Mix 2 contained 400 mM trehalose. Mix 3 and Mix 4 composed in 5 µl of the aqueous solution 352 mM Tris-HCl (pH 8.0 at 25° C.), 40 mM (NH$_4$)$_2$SO$_4$, 10 mM MgCl$_2$, 180 µM each dNTPs, 0.4 µM each primers, 360 µM Na$_4$PP$_i$, 2 units of polymerase, 0.04% Twee-20, 50 µg/ml BSA, 1 mM DTT, and 0.40% Ficoll-400. Moreover, Mix 3 contained 300 mM and Mix 4 contained 400 mM trehalose. Mix 5, Mix 6, and Mix 7 composed in 5 µl of the aqueous solution 352 mM Tris-HCl (pH 8.0 at 25° C.), 40 mM (NH$_4$)$_2$SO$_4$, 10 mM MgCl$_2$, 180 µM each dNTPs, 0.4 µM each primers, 360 µM Na$_4$PP$_i$, 2 units of polymerase, 0.04% Twee-20, 50 µg/ml BSA, 1 mM DTT. In addition, Mix 5 contained 200 mM trehalose and 0% Ficoll, Mix 6 contained 250 mM trehalose and 0.2% Ficoll, and Mix 7 contained 200 mM trehalose and 0.4% Ficoll.

TABLE 3

Stability test in the HIV gene

| Aqueous solution[a] | Performance | Before | Lyophilization | | | |
|---|---|---|---|---|---|---|
| | | | After | | | |
| | | | 0 days | 50° C. for 2 days | 50° C. for 4 days | 50° C. for 6 days |
| Mix 1 | Ct | 23.59 | 24.85 | 24.95 | 25.31 | 25.16 |
| | RFU | 540 | 440 | 460 | 440 | 540 |
| Mix 2 | Ct | 24.12 | 24.98 | 25.38 | 24.61 | 23.98 |
| | RFU | 540 | 450 | 460 | 480 | 540 |
| Mix 3 | Ct | 24.03 | 25.35 | 25.99 | 27.45 | 24.24 |
| | RFU | 580 | 440 | 410 | 380 | 400 |
| Mix 4 | Ct | 24.17 | 24.66 | 25.36 | 25.66 | 25.88 |
| | RFU | 580 | 520 | 480 | 440 | 440 |

Footnotes of Table 3.
[a]Mix 1, Mix 2, Mix 3, and Mix 4 were the same as in Table 2 except for HIV primers.

Example 4

A PAP assay was designed to amplify the rDNA gene (Table 1). SybrGreen I was used to emit real-time fluorescence signals.

The lyophilized integrated PAP composition was prepared as in Materials and Methods. Factors such as enzyme amount were tested (Table 4). After lyophilization, the samples were stored at 50° C. for 0, 1, 2, 3, 4 and 5 days. Before cycling, 0.2 ng of genomic DNA was added to 20 μl volume.

To assess the PAP amplification performance, Ct and RFU was measured. For 2 U and 1 U of polymerase, Ct and RFU showed the stability at 50° C. for five days. In addition, $T_m$ was also measured within 80-81° C., showing the specificity. Furthermore, when the enzyme amount decreased to 0.5 U, no efficient amplifications were observed.

TABLE 4

Stability test in the rDNA gene[a]

| Enzyme amount | Performance | After lyophilization | | | | | |
|---|---|---|---|---|---|---|---|
| | | 0 days | 50° C. for 1 day | 50° C. for 2 days | 50° C. for 3 days | 50° C. for 4 days | 50° C. for 5 days |
| 2 U | Ct | 25.84 | 25.05 | 24.63 | 24.84 | 24.64 | 24.54 |
| | RFU | 860 | 840 | 870 | 830 | 700 | 800 |
| 1 U | Ct | 25.82 | 25.61 | 26.26 | 26.87 | 26.42 | 25.83 |
| | RFU | 740 | 770 | 890 | 870 | 770 | 780 |

Footnotes of Table 4.
[a]Mix for the rDNA gene was 5 μl of the aqueous solution and composed 352 mM Tris-HCl (pH 8.0 at 25° C.), 40 mM $(NH_4)_2SO_4$, 10 mM $MgCl_2$, 180 μM each dNTPs, 0.4 μM each rDNA primers, 360 μM $Na_4PP_i$, 1 or 2 units of polymerase, 0.04% Twee-20, 50 μg/ml BSA, 1 mM DTT, 300 mM trehalose, and 0.4% Ficoll.

Example 5

Bidirectional-PAP assays were designed to amplify lung-cancer-specific mutants in the EGFR gene (Table 1). Sybr-Green I was used to emit real-time fluorescence signals.

The lyophilized integrated PAP composition was prepared as in Materials and Methods. PAP assays for three mutants of L858R, L861Q, and L790M were tested (Table 5). After lyophilization, the samples were stored at 50° C. for 1, 2, 3, 4 and 6 days. Before cycling, 1000 copies of the recombinant plasmid DNA in TE buffer was added to 20 μl volume.

To assess the PAP amplification performance, Ct and RFU was measured. For each mutant, Ct and RFU had similar values from 1 day to 6 days, showing the stability at 50° C. for six days. In addition, $T_m$ was also measured within 82-83° C., 80-81° C., and 85-86° C., showing the specificity.

TABLE 5

Stability test in the EGFR gene[a]

| EGFR mutant[a] | Performance | After lyophilization | | | | |
|---|---|---|---|---|---|---|
| | | 50° C. for 1 day | 50° C. for 2 days | 50° C. for 3 days | 50° C. for 4 days | 50° C. for 6 days |
| L858R | Ct | 22.09 | 21.36 | 21.77 | 22.10 | 21.72 |
| | RFU | 580 | 610 | 510 | 460 | 580 |
| L861Q | Ct | 22.46 | 22.52 | 23.14 | 23.01 | 22.91 |
| | RFU | 530 | 560 | 480 | 500 | 550 |

TABLE 5-continued

Stability test in the EGFR gene[a]

| EGFR mutant[a] | Performance | After lyophilization | | | | |
|---|---|---|---|---|---|---|
| | | 50° C. for 1 day | 50° C. for 2 days | 50° C. for 3 days | 50° C. for 4 days | 50° C. for 6 days |
| L790M | Ct | 23.31 | 22.80 | 23.09 | 23.16 | 22.84 |
| | RFU | 550 | 580 | 460 | 510 | 520 |

Footnotes of Table 5.
[a]Mix for the EGFR gene was 5 μl of the aqueous solution and composed 352 mM Tris-HCl (pH 8.0 at 25° C.), 40 mM $(NH_4)_2SO_4$, 10 mM $MgCl_2$, 180 μM each dNTPs, 0.4 μM each EGFR primers, 360 μM $Na_4PP_i$, 2 units of polymerase, 0.04% Twee-20, 50 μg/ml BSA, 1 mM DTT, 300 mM trehalose, and 0.4% Ficoll.

REFERENCE

1. Liu, Q., and Sommer, S. S. (2000). Pyrophosphorolysis-activated polymerization (PAP): application to allele-specific amplification. BioTechniques 29, 1072-1080.
2. Liu, Q., and Sommer, S. S. (2004). PAP: detection of ultra rare mutations depends on P* oligonucleotides: "sleeping beauties" awakened by the kiss of pyrophosphorolysis. Human mutation 23, 426-436.
3. Liu, Q., and Sommer, S. S. (2004). Detection of extremely rare alleles by bidirectional pyrophosphorolysis-activated polymerization allele-specific amplification (Bi-PAP-A): measurement of mutation load in mammalian tissues. BioTechniques 36, 156-166.
4. Liu, Q., and Sommer, S. S. (2002). Pyrophosphorolysis-activatable oligonucleotides may facilitate detection of rare alleles, mutation scanning and analysis of chromatin structures. Nucleic acids research 30, 598-604.
5. Deutscher, M. P., and Kornberg, A. (1969). Enzymatic synthesis of deoxyribonucleic acid. 28. The pyrophosphate exchange and pyrophosphorolysis reactions of deoxyribonucleic acid polymerase. The Journal of biological chemistry 244, 3019-3028.
6. Nazarenko, I., Lowe, B., Darfler, M., Ikonomi, P., Schuster, D., and Rashtchian, A. (2002). Multiplex quantitative PCR using self-quenched primers labeled with a single fluorophore. Nucleic acids research 30, e37.

The invention claimed is:

1. A method for lyophilizing integrated composition for PAP which is performed with a thermo-cyclying procedure comprising:
   a) providing integrated composition in an aqueous solution comprising a mixture of I) a reaction buffer, 3' blocked primers which contain 2', 3' dideoxynucleotides at the 3' ends and which are activated by pyrophosphorolysis activity of polymerase to produce a 3' unblocked primers and then extended by polymerization activity of polymerase in PAP amplification, deoxynucleotide triphosphates, pyrophosphate which is a substrate and pre-exists before PAP starts amplification, a fluorescent dye, and a nucleic acid polymerase and which catalyzes two serially coupled reactions of pyrophosphorolysis and polymerization in PAP amplification, but not nucleic acid template, and II) a non-reducing disaccharide, and
   b) lyophilizing the aqueous solution into dried integrated composition before PAP starts amplification,
   whereby the integrated composition can be easily stored and manipulated.

2. The method according to claim 1, wherein the reaction buffer comprises 176 mM Tis-HCl (pH 8.0 at 25° C.), 20 mM $(NH_4)_2SO_4$, and 2.4-5 mM $Mg^{++}$.

3. The method according to claim 1, wherein the deoxynucleotide triphosphates, and pyrophosphate which pre-exists before PAP starts amplification, are 50 or 90 um each dATP, dTTP, dGTP, and dCTP, 180 uM $Na_4O_7P_2$ or their analogs, whereby they provide substrates for polymerization and pyrophosphorolysis.

4. The method according to claim 1, wherein the disaccharide comprises trehalose, sucrose, maltose, cellobiose, lactose, or lactulose at concentrations from 200 mM to 400 mM.

5. The method according to claim 1, wherein the aqueous solution further comprises 100 ng/ml BSA.

6. The method according to claim 1, wherein the aqueous solution further comprises a polyol selected from a group consisting of Ficoll, Dextran, polyethylene glycol (PEG), and Polyvinylpyrrolidone (PVP) at concentration 0.2%.

7. The method for lyophilizing integrated composition for PAP according to claim 1, further comprising a step: c) solubilizing the lyophilized integrated composition by addition of a nucleic acid template in an aqueous solution.

8. The method according to claim 1, wherein the trehalose disaccharide concentrations are preferred from 200 mM to 400 mM.

9. The method for lyophilizing integrated composition for PAP according to claim 1, further comprising a step: d) performing PAP amplification through a thermo-cyclying procedure which includes steps of denaturation.

* * * * *